United States Patent [19]

Winicki

[11] 4,029,094
[45] June 14, 1977

[54] DEVICE FOR REGULATING PERFUSION FLOWRATE

[75] Inventor: Bernard Winicki, Neuilly sur Seine, France

[73] Assignee: Union Chimique Continentale - U.C.C. Societe Anonyme, Puteaux, France

[22] Filed: Feb. 17, 1976

[21] Appl. No.: 658,718

[30] Foreign Application Priority Data

Mar. 4, 1975  France .............................. 75.06677

[52] U.S. Cl. ........................ 128/214 F; 128/214 E; 128/DIG. 12; 128/DIG. 13; 222/55

[51] Int. Cl.² .......................................... A61M 5/14

[58] Field of Search .... 128/214 F, 214 E, DIG. 12, 128/DIG. 13, DIG.16, 225, 230, 273, 274, 227, 214.2; 222/55, 61, 76, 52; 137/486, 209; 417/118, 139

[56] References Cited

UNITED STATES PATENTS

| | | | |
|---|---|---|---|
| 3,014,481 | 12/1961 | Rumble | 128/214 F |
| 3,091,239 | 5/1963 | Moeller | 128/214 F |
| 3,640,276 | 2/1972 | Dancy | 128/214 F |
| 3,648,694 | 3/1972 | Mogos et al. | 128/214 F |
| 3,736,930 | 6/1973 | Georgi | 128/214 E |

FOREIGN PATENTS OR APPLICATIONS 1,573,076  3/1970  Germany .......................... 137/486

Primary Examiner—Robert W. Michell
Assistant Examiner—Michael H. Thaler
Attorney, Agent, or Firm—Browdy and Neimark

[57] ABSTRACT

The flow rate regulation, notably of a rapid perfusion flow rate, is effected by regulating the pressure in the perfusion reservoir by the application of a voltage to a compressor, which increases the flow rate of the liquid in the perfusion tubing by sending pressurized air into the reservoir. The latter is at atmospheric pressure when no voltage is applied to the compressor. The device comprises the combination of a perfusion reservoir and a compressor which causes the pressure in said reservoir to vary. Consequently the flow rate of the perfusion liquid delivered by the latter into the perfusion tubing varies. The compressor is governed by a differential voltage resulting from the comparison by an electronic circuit of the real value with the desired value of the flow rate in the perfusion tubing. This differential voltage is applied to the compressor which then sends compressed air into the perfusion reservoir.

5 Claims, 2 Drawing Figures

DEVICE FOR REGULATING PERFUSION FLOWRATE

BACKGROUND OF THE INVENTION

1. Field of the Invention

The present invention relates to a novel method for regulating perfusion flow rate and to a novel device for regulating perfusion flow rate.

As is known, the liquid to be perfused is contained in a reservoir which flows through a tubing directly into the vein of the patient, into which a perfusion needle is inserted.

2. Description of the Prior Art

Known perfusion flow rate control devices are usually peristaltic pumps whose flow rate is controlled essentially by roller systems.

However, these peristaltic pumps have numerous drawbacks. In these known devices, even if the flow rate is monitored it is not servocoupled. Moreover, peristaltic pumps can cause flattening of the perfusion reservoir. On the other hand, the peristaltic force is continuously exerted at the same place and over the same distance, so that it causes the customary PVC tubing to loose its elasticity, resulting in its premature wear. This has the result that the use of peristaltic pumps for controlling perfusion flow rate necessitates the use of special tubings having exceptional strength.

In addition, the flow rate is not measured directly: it is equal to the speed of the pump, which makes the calibration of the pump necessary, and consequently, it is subject to the errors or approximations of such calibration.

OBJECTS AND SUMMARY OF THE INVENTION

It is an object of the present invention to provide a method and a device which not only monitor, but also regulate perfusion flow rate.

It is another object to provide a device which permits acceleration of flow rates in all cases of urgency where rapid perfusion is required.

It is a further object to provide a perfusion flow rate regulating device which can be used in association with conventional perfusion tubing.

Other objects and advantages will become apparent from the description which follows.

According to the present invention there is provided a method for regulating perfusion flow rate, notably of a rapid perfusion flow rate, characterized in that the regulation of the flow rate is effected by regulating the pressure in the perfusion reservoir by the application of a voltage to a compressor, which increases the flow rate of the liquid in the perfusion tubing, by sending air under pressure into the reservoir, the latter being at atmospheric pressure when no voltage is applied to the compressor.

According to another object of the present invention there is provided a device for regulating perfusion flow rate, notably a rapid perfusion flow rate, characterized by the combination with a perfusion reservoir of a compressor which causes the pressure in said reservoir to vary and consequently the flow rate of the perfusion liquid delivered by the latter into the perfusion tubing, under the effect of a differential voltage resulting from the comparison by an electronic circuit known in itself, of the actual value with the desired value of the flow rate in the perfusion tubing, which differential voltage is applied to the compressor which then sends compressed air into the perfusion reservoir.

According to an advantageous feature of the invention, the differential voltage is obtained by comparison of the output voltage corresponding to the flow rate desired, with a voltage calibrated experimentally.

According to another advantageous feature of the invention, the differential voltage is obtained by comparison of the output voltage, proportional to the flow rate of the perfusion liquid in the perfusion tubing, measured by a flow meter with the voltage representing the value of the desired flow rate.

According to another feature of the present invention, the regulation of the pressure in the perfusion reservoir is effected by means of the air intake normally associated with the reservoir and with the perfusion tubing, which air intake is connected, on the one hand, to the compressor and, on the other hand, to a hollow body such as a needle, for example, which extends into the reservoir to send therein regulating pressurized air, coming from the compressor.

According to another feature of the invention, a flow rate sensor, which is associated with the perfusion tubing, cooperates with the flow meter for measuring the flow rate in said tubing.

According to yet another feature of the invention, communication between the compressor and the reservoir is established by means of an electrovalve.

Another particular feature of the invention provides for the interposition of a sterilizing filter for the air between the compressor and the reservoir.

Yet another particular feature of the invention provides for the opening of the hollow body for injecting air into the reservoir, above the level of the liquid contained in said perfusion reservoir.

Besides the foregoing features, the invention comprises other features which will emerge from the description which follows.

The invention relates more particularly to methods and devices for regulating perfusion flow rate, according to one or more of the foregoing features, as well as to means adapted to the application of these methods and the production of these devices, and equipment in which these methods and/or these devices is included.

BRIEF DESCRIPTION OF THE DRAWINGS

The invention will be better understood by means of the additional description which follows, with reference to the accompanying drawings in which.

It must be understood, however, that these drawings and the corresponding descriptions are given solely by way of illustration of the invention, of which they do not constitute in any way a limitation.

DESCRIPTION OF PREFERRED EMBODIMENTS

Figure 1:
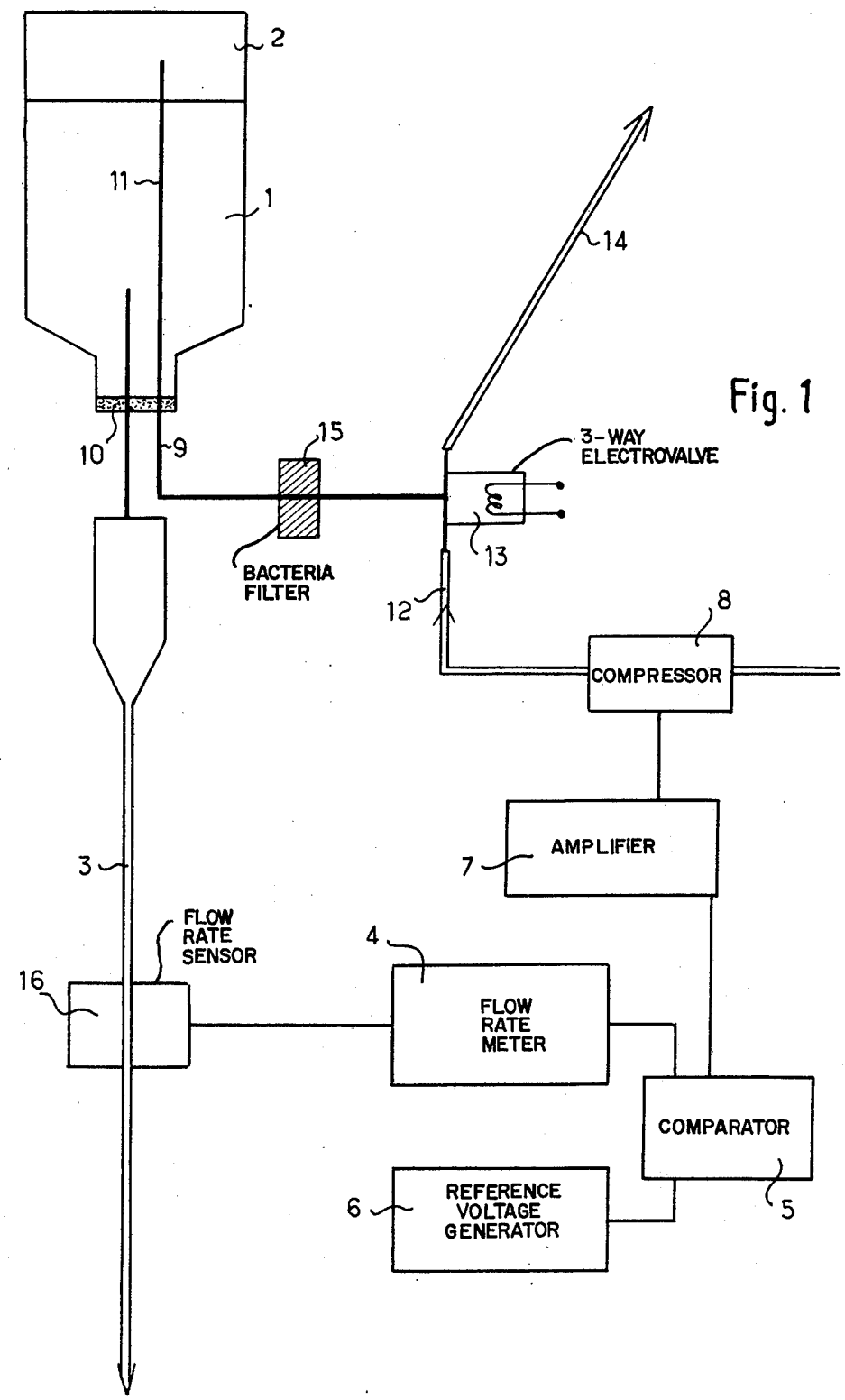
FIG. 1 represents the block diagram of a perfusion flow rate regulating device according to the present invention.

In the block diagram shown by way of non-limiting example in FIG. 1, the perfusion liquid 1 is contained in the reservoir 2 and flows through a tube 3 directly into the vein of the patient. The tube 3 is of the type customarily used for perfusion, for example of flexible PVC.

The flow rate of the liquid in the tube 3 is measured by a flowmeter 4, whose output voltage, proportional to the flow rate, is compared by the comparator 5, to a voltage corresponding to the desired flow rate, delivered by a voltage generator 6.

It is advantageous to use in the device according to the present invention a transit time flowmeter, since the liquids delivered are not necessarily conducting, they do not include suspended particles and they flow in a tube; moreover, transit time flowmeters emit a signal in the case of the passage of an air bubble in the tube, so that it is advantageous to associate a warning device with them which stops the regulating device according to the invention.

For reasons of economy or if high accuracy in measuring the flow rate is not sought, it is possible to leave out the flowmeter and to replace it by a continuous voltage calibrated experimentally.

Whatever the method chosen to measure the voltage corresponding to the flow rate in the tube 3, the voltage corresponding to the difference between the value of the actual flow rate and the value of the desired flow rate, is amplified by the amplifier 7 and is applied to a miniature compressor 8 whose rotary speed it controls. Under the effect of the voltage thus applied to it, the compressor sends air under pressure into the reservoir 2, thus driving the liquid contained in said reservoir, into the tube 3. The air under pressure coming from the compressor 8, arrives at the reservoir 2 through the following means:

The air intake 9 which includes, in the usual manner, the perfusion reservoir 2, is connected, at the level of the stopper 10 of the reservoir 2, to a hollow body 11 such as a needle, for example, which is sufficiently long for its free end to open above the level of the liquid contained in the reservoir 2, in order to avoid production of air bubbles in the perfusion liquid. At its outer end, the air intake 9 is connected to the tube 12 in which compressed air coming from the compressor 8 circulates.

It is advantageous, but not indispensable, to insert between the air intake 9 and the compressed air tube 12, a three-way valve, such as the electrovalve 13, for example, which, according to the requirements, puts the air intake 9 into communication with the compressed air tube 12, or puts the air intake 9 into communication with atmospheric pressure, through the exhaust tube 14.

Preferably, but not by way of limitation, a valve-type compressor, capable of producing a pressure of the order of 20 to 500 mm of Hg in the perfusion reservoir is used and advantageously a pressure of the order of 70 to 300 mm of Hg.

It is advantageous to insert between the compressed air tube 12 and the air intake 9, a bacteria filter 15, which has the role of sterilizing the air under pressure coming from the compressor 8, before its introduction into the perfusion liquid 1.

A flow rate sensor 16 associated with the perfusion tube 3, cooperates with the flowmeter 4 to measure the actual flow rate in the tube 3. It is advantageous to use a flow rate sensor of the ultrasonic type, which surrounds the tube 3.

The device which has just been described with reference to FIG. 1, is different from those used for the regulation of slow perfusion flow rates, generally comprised between 1 and 180 drops/minute; in fact, it enables flow rates of 5 to 100 ml/minute to be regulated which may prove to be necessary to respond to emergencies where rapid perfusion is required.

The device according to the present invention and of which an embodiment has just been described with reference to FIG. 1 may be used alone, in which case it can advantageously be placed in a box fixed to the lower part of the hanger which normally supports the perfusion reservoir.

However, it is particularly advantageous to use it in association with a regulator for low perfusion flow rates, which permits the provision, in a single apparatus, of regulating means for low perfusion flow rates and regulating means for accelerated perfusion flow rates necessary in the case of an emergency.

Figure 2:
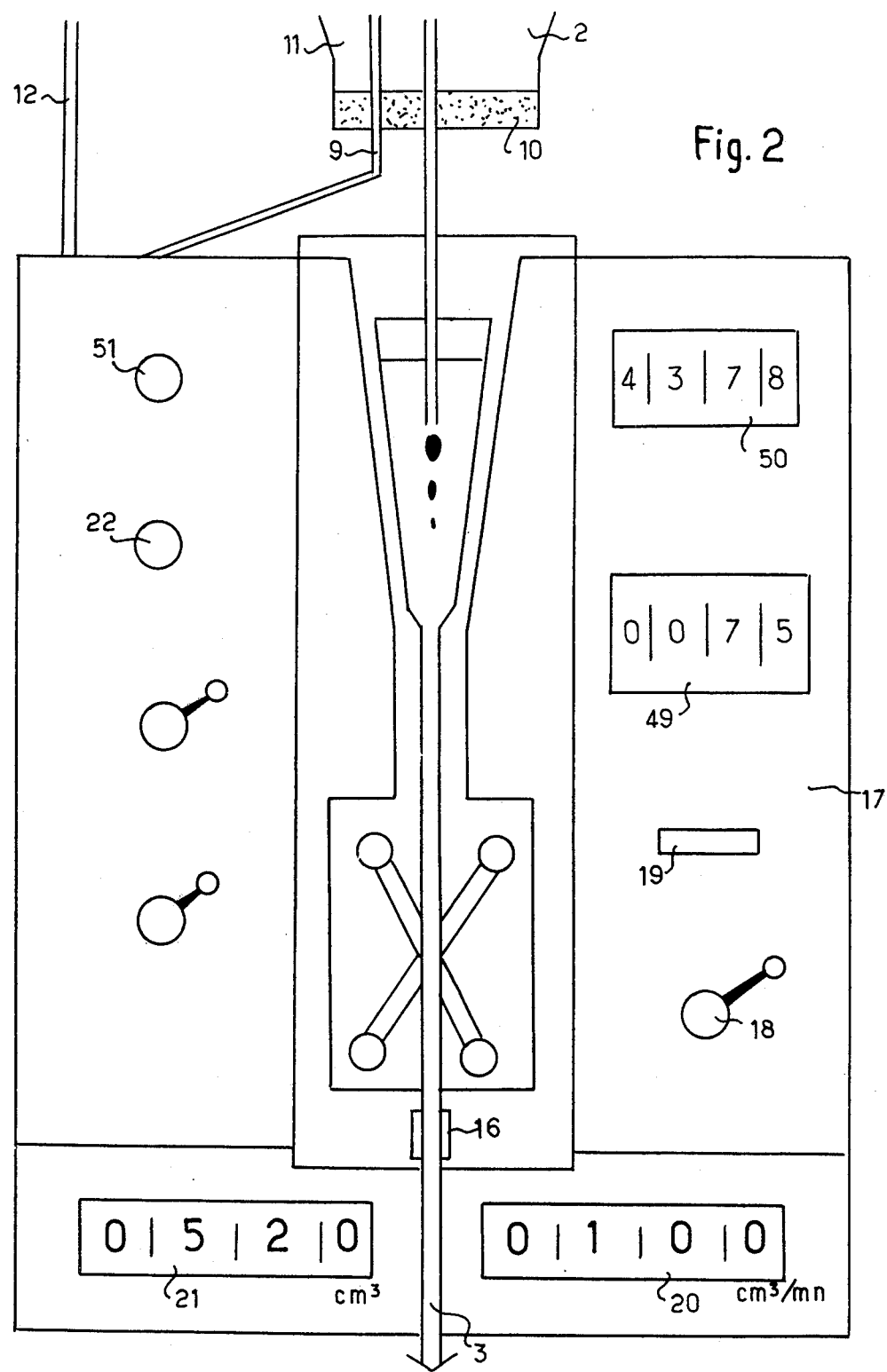
FIG. 2 represents one embodiment of an apparatus including the device according to the present invention.

The coupling of the two regulators in the same box, of the type described and claimed in the pending U.S. patent application Ser. No. 629,239 of Nov. 6, 1975, in the name of the present asignee is shown diagrammatically by way of nonlimiting example, in FIG. 2 of the accompanying drawings.

The flow rate sensor 16 is placed in a clamp fixed to the lower part 17 of the unit which contains the reservoir 2 of the perfuser.

The switch 18 of the rapid perfusion flow rate regulating device according to the present invention, is called "emergency switch." When it is actuated, the clamp of the low flow rate regulator (not shown) for example of the type described in the aforementioned U.S. Patent Appln. opens, the low flow rate regulator stops, the air intake 9 is connected to the compressor 8 and the latter sends air under pressure into the reservoir 2 of the perfusate, as described above. The regulation of high flow rates is then ensured by the flow rate sensor 16 placed in the clamp and by the whole of the device according to the invention.

The box 17 contains the electronic assemblies of the low flow rate regulating device described in the prior art and of the high flow rate perfusion regulating device. It carries a control and display panel which includes a stop-go 19, a display pick-up 49 of the desired preselected number of drops, and integrating pick-up 50 of the number of drops, a luminous signalling device 51 which lights up on the passage of each drop and display pick-up 20 of the preselected desired flow rate, in $cm^3$/minute, for high flow rates, a display pick-up 21 for the volume to be perfused, in $cm^3$, for high flow rates, and a luminous signalling device 22 which lights up in the case of a high flow rate, in a continuous jet.

From the foregoing description, it will be clear that whatever the mode of operation, embodiment and application adopted, methods and devices for regulating a perfusion flow rate are obtained, which have with respect to methods and devices for the same purpose, previously known, important advantages, among which are included the possibility of regulating, and not only checking, flow rates of rapid perfusion, and the possibility of coupling regulating devices for low flow rates and for high flow rates of perfusion.

As emerges from the foregoing, the invention is in no way limited to those of its modes of operation, embodiments and types of application, which have just been described more explicitly; it encompasses, on the contrary, all modifications which can occur to the technician skilled in the art, without departing from the field, or from the scope of the present invention, and notably, the application of the method and of the device for regulating rapid flow rates, to other fields than the medical and medicosurgical fields, and notably to chemical, biochemical, and biological etc. laboratory techniques.

I claim:

1. A device for regulating perfusion flow rate, notably of a rapid perfusion flow rate, comprising:
    an air compressor;
    an air pipe fed by said compressor;
    a perfusion reservoir, air-fed by said pipe;
    a perfusion tubing, liquid-fed by said reservoir;
    a flow rate sensor connected to said tubing;
    a flow rate meter driven by said sensor and furnishing a measuring voltage;
    reference voltage generator means for furnishing a perdetermined reference voltage corresponding to the desired flow rate;
    comparator means for comparing said measuring voltage with said reference voltage and for furnishing a differential voltage; and
    control means, driven by said differential voltage, for controlling the speed of said compressor relative to said differential voltage.

2. A device in accordance with claim 1, wherein said flow rate sensor is for measuring continuous flow in said tubing.

3. A device in accordance with claim 1 further including electrovalve means for controlling flow of air in said air pipe.

4. A device in accordance with claim 1 further including a compressed air sterilizing filter interposed in said air pipe between said air compressor and said perfusion reservoir.

5. Flow rate measuring apparatus including the rapid perfusion flow rate regulation device in accordance with claim 1, coupled to a low flow rate perfusion regulating means.

* * * * *